(12) United States Patent
Muir et al.

(10) Patent No.: US 12,168,671 B2
(45) Date of Patent: Dec. 17, 2024

(54) PHOSPHOHISTIDINE MIMETICS AND ANTIBODIES TO SAME

(71) Applicant: The Trustees of Princeton University, Princeton, NJ (US)

(72) Inventors: Tom W. Muir, Princeton, NJ (US); Rob C. Oslund, Princeton, NJ (US); Jung-Min Kee, Ulsan (KR)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 17/707,330

(22) Filed: Mar. 29, 2022

(65) Prior Publication Data
US 2022/0220134 A1    Jul. 14, 2022

Related U.S. Application Data

(62) Division of application No. 16/135,396, filed on Sep. 19, 2018, now abandoned, which is a division of application No. 15/026,670, filed as application No. PCT/US2014/058758 on Oct. 2, 2014, now Pat. No. 10,351,581.

(60) Provisional application No. 61/885,657, filed on Oct. 2, 2013.

(51) Int. Cl.
| | | |
|---|---|---|
| *C07F 9/6503* | (2006.01) | |
| *C07K 16/44* | (2006.01) | |
| *G01N 33/53* | (2006.01) | |

(52) U.S. Cl.
CPC .......... *C07F 9/65031* (2013.01); *C07K 16/44* (2013.01); *G01N 33/5308* (2013.01); *G01N 2800/26* (2013.01)

(58) Field of Classification Search
CPC . C07K 16/44; C07F 9/65031; G01N 33/5308; G01N 2800/26
See application file for complete search history.

(56) References Cited

U.S. PATENT DOCUMENTS

| | | |
|---|---|---|
| 9,765,154 B2 | 9/2017 | Muir et al. |
| 9,957,294 B2 | 5/2018 | Stankova et al. |
| 10,053,476 B2 | 8/2018 | Jackson et al. |
| 10,351,581 B2 | 7/2019 | Muir et al. |
| 2016/0207948 A1 | 7/2016 | Jackson et al. |

OTHER PUBLICATIONS

Midura et al. Optically active α,β-unsaturated α-phosphoryl sulfoxides. Multifunctional reagents for the asymmetric Michael and Diels-Alder reaction. Phosphorous, sulfur, and silicon and related elements 1994, vol. 95, pp. 397-398. Abstract with excerpt from STN search supplied. (Year: 1995).*
PubChem. Compound Summary for CID 69724635; create date Dec. 1, 2012 (entire document).
PubChem. Compound Summary for CID 54200281; create date Dec. 4, 2011 (entire document).

* cited by examiner

*Primary Examiner* — Shafiqul Haq
(74) *Attorney, Agent, or Firm* — MEAGHER EMANUEL LAKS GOLDBERG & LIAO, LLP

(57) ABSTRACT

Provided are phosphonopyrazole-based phosphohistidine analogs that are useful as haptens for the preparation of immunogens, immunogens that include these haptens linked to carrier molecules, antibodies thereto and uses of these antibodies, haptens, immunogens and phosphohistidine analogs.

1 Claim, 5 Drawing Sheets

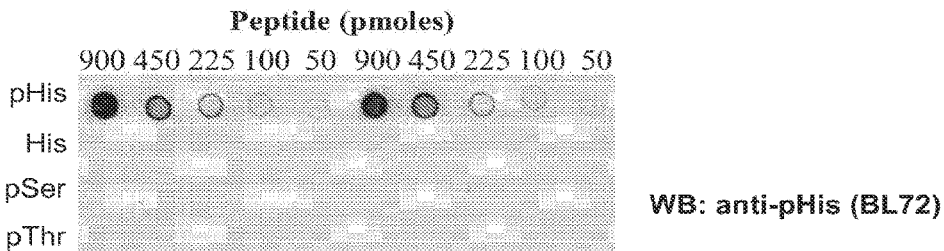

FIG. 2A  WB: anti-pHis (BL72)

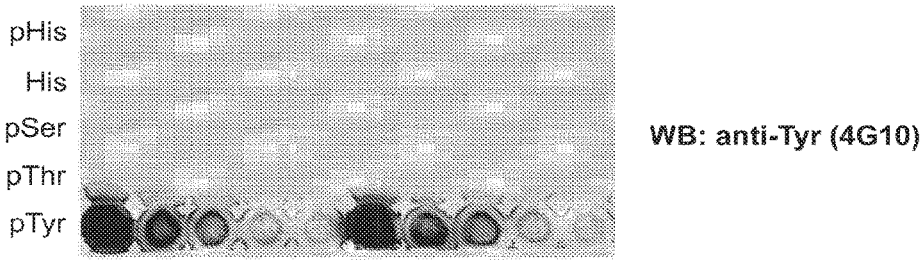

FIG. 2B  WB: anti-Tyr (4G10)

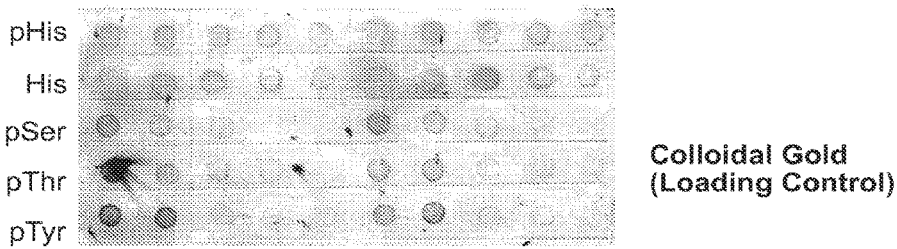

FIG. 2C  Colloidal Gold (Loading Control)

FIG. 2D

| Gene Name | [a]Tryptic Peptide Sequence |
|---|---|
| Putative PTS system EIIA component (FrvR) | LAIPXCWSEQER |
| PTS system mannose-specific EIIAB component (ManX) | LIXGQVATR |
| PTS system N-acetylglucosamine EIICBA component (NagE) | GAEIVVXMGIDTVALEGK |
| Aerobic respiration control sensor protein (ArcB) | GIVEEGXK |
| Fumarate sensor histidine kinase (DcuS) | SXEFMNK |
| Phosphate regulon sensor protein (PhoR) | NFFANVSXELR |
| Succinyl-CoA synthetase subunit alpha (SucD) | MCXAGAIIAGGK |
| 2,3-bisphosphoglycerate-dependent phosphoglycerate mutase (GpmA) | XGESQWNK |
| Nucleoside diphosphate kinase (Ndk) | ADYADSLTENGTXGSDSVESAAR |

[a]X = His, pHis, pSer, pThr, pTyr

BL72 (pPye) Serum Displays Superior Affinity for Purified pHis Proteins

WB: 5667 (α-pHis 1.0)

WB: BL72 (pPye)

WB: H70 (pPye)

Coomassie:
5667 (α-pHis 1.0)

Coomassie:
CST-BL72 (pPye)

Coomassie:
CST-H70 (pPye)

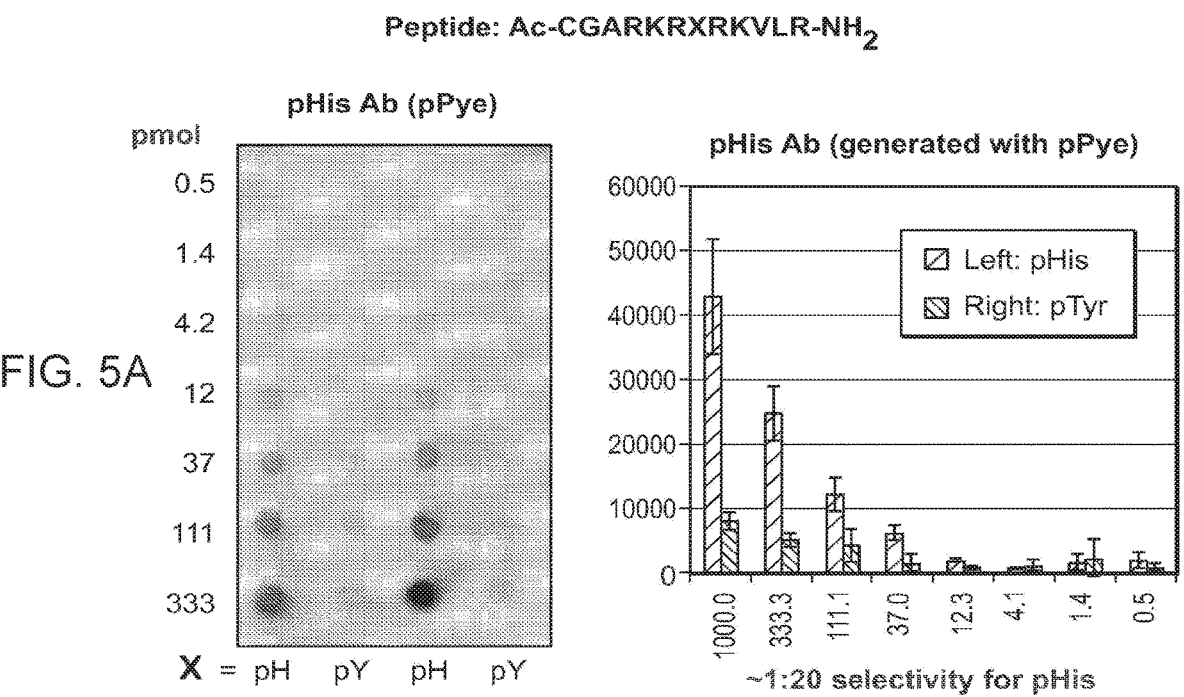
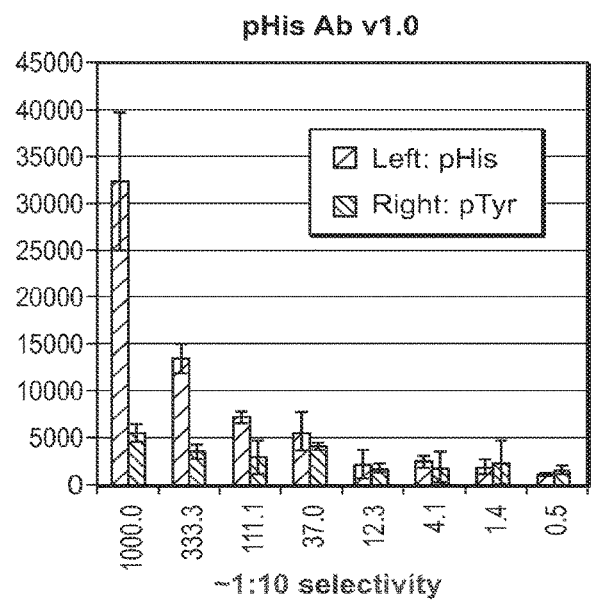
FIG. 5A
FIG. 5B
FIG. 5C

PHOSPHOHISTIDINE MIMETICS AND ANTIBODIES TO SAME

RELATED APPLICATIONS

This application is a divisional of U.S. application Ser. No. 15/026,670, which is the U.S. national phase of International Patent Application No. PCT/US2014/058758, filed Oct. 2, 2014 and claims the benefit of the filing date of U.S. provisional application No. 61/885,657, which was filed Oct. 2, 2013, The disclosures of these applications are incorporated by reference herein in its entirety entireties.

STATEMENT AS TO FEDERALLY SPONSORED RESEARCH

This invention was made with government support under Grant No. 5R01GM095880 awarded by the National institutes of Health (NIGMS) and Grant No. F32CA167901-02 awarded by the National Institutes of Health (NCI). The government has certain rights in the invention.

FIELD OF THE INVENTION

The present invention relates to phosphohistidine analogs that are useful as haptens for the preparation of immunogens, immunogens that include these haptens linked to carrier molecules, antibodies thereto and uses of these antibodies, haptens, immunogens and phosphohistidine analogs.

BACKGROUND

Protein phosphorylation is one of the most common and extensively studied posttranslational modifications. Relatively little is known, however, about phosphorylation of histidine residues, which occurs at the imidazole nitrogens. While some anti-phosphohistidine antibodies have been described, they can cross-react with antibodies to other phosphorylated amino acids and/or do not bind phosphohistidines with desired affinity.

SUMMARY

The invention is based in part on new pHis analogs that are chemically stable and which have been used as haptens and immunogens to generate specific anti-pHis antibodies that bind with high affinity and specificity. The antibodies are useful, inter alia, for investigating the role of pHis in physiological functions.

Accordingly, in one aspect, the invention is directed to a phosphonopyrazole of formula I:

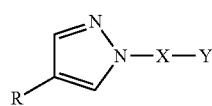

(I)

wherein
R is

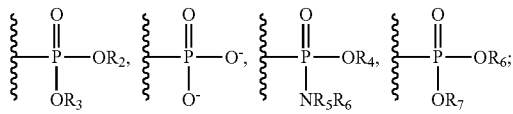

$R_2$, $R_3$, $R_4$, $R_5$, $R_6$, $R_7$, and $R_8$ are each independently H, alkyl, alkenyl, cycloalkyl, cycloalkylalkyl, aryl, arylalkyl, heterocyclyl, heterocyclylalkyl, or a phosphate protecting group;

X is a chemical bond or a linker group selected from alkylene, alkenylene, alkynylene, cycloalkylene, cycloalkylenealkylene, cycloalkenylene, cycloalkenylenealkylene, heterocyclylene, heterocyclylenealkylene, —(O—$CH_2$—$CH_2$)$_n$—, or —($CH_2$)$_q$— where one of the —$CH_2$— groups is replaced by —O—;

n is 1-100;

q is 1-6;

Y is H, —$OR_9$, —$NR_9R_{10}$, —$SR_9$, —$COOR_9$, —C(O)$NR_9R_{10}$, —NHJ or —C(O)Q;

$R_9$ and $R_{10}$ are each independently H, alkyl, alkenyl, alkynyl, cycloalkyl, cycloalkylalkyl, aryl, arylalkyl, heterocyclyl, heterocyclylalkyl;

J is an amino protecting group; and

Q is a carboxylic acid protecting group.

Another aspect of the present invention is directed to a hapten comprising the phosphonopyrazole of formula I as disclosed herein. The hapten can be conjugated to carrier material to provide immunogens for anti-pHis antibody production and conjugates.

In still further aspects, the present invention provides an immunogen comprising a hapten of the present invention coupled to an antigenicity conferring carrier material. The carrier material may be, for example, a protein, a protein fragment, a synthetic polypeptide or a semi-synthetic polypeptide.

In a still further aspect, the present invention is directed to an isolated antibody raised against the immunogen of the present invention. This antibody recognizes phis as but does not recognize non-phosphorylated His or peptides that are not phosphotylated or amino acids which are not histidine which are phosphorylated or peptides which are phosphorylated on amino acid residues other than histidine and not on histidine.

In a still further aspect, the present invention comprises a conjugate comprising the hapten of the present invention covalently bonded to a detectable labeling agent. For example, the labeling agent is selected from an enzyme, a luminescent substance, a radioactive substance or mixture thereof. In one embodiment, the labeling agent is an enzyme, such as a peroxidase, e.g., horseradish peroxidase. Alternatively or additionally, the luminescent substance may be a bioluminescent, chemiluminescent or fluorescent material.

In a further aspect, the present invention provides a process of preparing the antibodies, the process comprising the steps of immunizing an animal, such as a vertebrate animal, e.g., a mammal, by repeated administration of the immunogen of the present invention and collecting the resulting serum from the immunized animal and isolating the antibodies from the serum using techniques known to one of ordinary skill in the art. In another embodiment, the present process comprises exposing the immunogen of the present invention to a phage-display library expressing antibodies and isolating the phages and the antibodies that specifically bind to the immunogen using techniques known to one of ordinary skill in the art. In another aspect, the present invention relates to a process which comprises fixing these serum antibodies to a backing substrate, such as, for example, a solid support, e.g., polypeptide. The antibodies may be monoclonal or polyclonal. The antibodies of the present invention do not recognize non-phosphorylated proteins or amino acids, but do recognize phosphorylated histidine residues, but not other phosphorylated amino acids.

In a further aspect, the invention comprises a method of detecting a phosphorylated histidine in a biological sample comprising contacting the sample with the conjugate of the present invention or a mixture thereof and with antibodies of the present invention or a mixture thereof, detecting or determining bound conjugate and deducing from a calibration curve the presence or amount of phosphopolypeptides containing a phosphorylated histidine in the biological sample. The biological sample is usually a solution, e.g., serum or urine.

The present invention includes a kit for detecting phosphorylated polypeptides comprised of at least one phosphorylated histidine residue in a biological sample, the kit including the one or more of the haptens and the antibodies of the present invention or a mixture thereof. The kit may optionally include instructions for use of haptens and the antibodies for detecting and or determining the presence of phosphorylated polypeptides comprised of at least one phosphorylated histidine residue.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWING

FIG. 2A-D shows a dot blot analysis of a library of phosphopeptides as identified in D. A) Dot blot analysis of the library probed with anti-pHis (BL72). B) Dot blot analysis of the library probed with anti-pTyr (4010° C.) Dot blot analysis of the library probed with colloidal gold (control). D) Identity of peptides making up the library.

FIG. 5A-C shows a dot blot analysis of a Histone H4-derived peptide sequence Ac-CGARKR, XRKVLR-NH$_2$ (where X is pHis or pTyr) (SEQ ID NO:1). A) 0.5, 1.4, 4.2, 12, 37, 111, and 333 parole of peptide was spotted in duplicate on a membrane and probed with pPye-elicited antisera. B) Binding was 20-fold more selective for pHis than for pTyr. Antisera raised against pTze (pHis Ab v1.0) was only 10-fold more selective for pHis than for than pTyr.

DEFINITIONS

Figure 1:
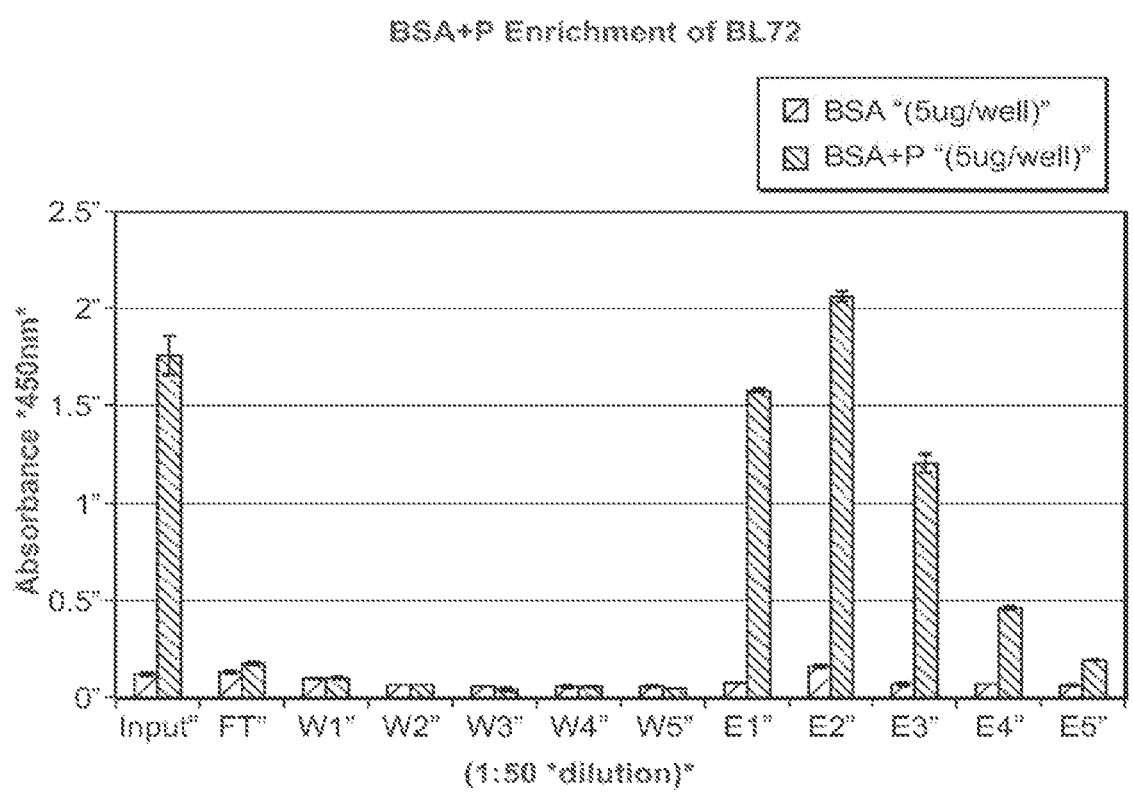
FIG. 1 shows an ELISA analysis of affinity-purified anti-pHis antibodies (BL72) raised against the pPye hapten. Crude antiserum from a rabbit immunized with a pPye-KLH immunogen was affinity purified using phosphorylated BSA attached to agarose beads. The input, flow through (FT), wash fractions (W1, W2, W3, W4, W5) and elution fractions (E1, E2, E3, E4, E5) were collected and used for the analysis.

Throughout the present specification the following definitions are to be understood.

As used herein, the term "alkyl", when used alone or in combination with other groups, refers to an alkyl group containing 1-15 carbon atoms. The alkyl group may be straight chained or branched. The alkyl groups may be a lower alkyl group containing 1-6 carbon atoms. Examples of alkyl groups include methyl, ethyl, n-propyl, isopropyl, n-butyl, isobutyl, sec-butyl, t-butyl, n-pentyl, isopentyl, neopentyl, 2-methylpentyl, n-hexyl, 2, 2-dimethylpentyl, 3-methylpentyl, 2,2-dimethylbutyl, 2,3-dimethylbutyl, heptyl, octyl, nonyl, decyl and the like.

The term "alkoxy", when used alone or in combination with other groups, refers to a terminal oxy containing alkyl group, as defined above such as methoxy, ethoxy, propoxy, isopropoxy and the like.

The term "cycloalkyl", when used alone or in combination with other groups, refers to the cyclic analog of an alkyl group, as defined herein, which contains 3 to 10 ring carbon atoms. It may be monocyclic or bicyclic or tricyclic. The cycloalkyl groups contain no ring saturation, although as described below, they may have unsaturated substituents. The cycloalkyl groups include cycloalkyl groups containing 3, 4, 5 and 6 ring carbon atoms. Examples of cycloalkyl include cyclopropyl, cyclobutyl, cyclopentyl, cyclohexyl, cycloheptyl, cyclooctyl, cyclodecyl, adamantyl, and the like.

The terms "alkenyl" and "alkynyl", when used alone or in combination with other groups, refer to mono- or polyunsaturated aliphatic hydrocarbon radicals containing from two to 15 carbon atoms, containing at least one double or triple bond, respectively.

"Alkenyl" and "alkynyl" refer to both branched and unbranched alkenyl and alkynyl groups, respectively. The alkenyl and alkynyl groups include straight chained alkenyl or alkynyl groups containing from two to eight carbon atoms and branched alkenyl or alkynyl groups containing from five to ten carbon atoms. The alkenyl and alkynyl groups also include alkenyl and alkynyl groups containing from two to six carbon atoms and branched alkenyl and alkynyl groups containing from 5 to eight carbon atoms. Examples of alkenyl groups include ethenyl, 2-propenyl, 1-propenyl, 2-methyl-1-propenyl, 1-butenyl, 2-butenyl, 1-pentenyl, 2-pentenyl, 3-pentenyl, allyl, 1,3-butadienyl, 1,3-dipentenyl, 1,4 dipentenyl, 1-hexenyl, 1,3-hexenyl, 1,4-hexenyl, 1,3,5-trihexenyl, 2,4-dihexenyl, and the like.

Examples of alkynyl include ethynyl, 1-propynyl, 2-propynyl, 1 butynyl, 2-butynyl, 2-methyl-1-butynyl, 1-pentynyl, 2-pentynyl, 3-pentynyl, 3-methyl-1-pentynyl, 2-methyl-1-pentynyl, 1-hexynyl, 2-hexynyl, 3-hexynyl, and the like. The alkenyl and alkynyl groups contain at least one double bond or one triple bond, respectively. In another embodiment, they each may contain up to 4 carbon-carbon multiple bonds, for example, 1, 2, 3, or 4, double bonds or triple bonds, respectively. The double bonds in the alkenyl groups may be conjugated, as in 1,3-butadienyl, or non-conjugated, as in 1,4-di pentenyl.

The term "cycloalkenyl", when used alone or in combination with other groups refers to the cyclic analog of an alkenyl group containing from 3 to 10 carbon atoms. The cycloalkenyl group contains from 3 to 10 ring carbon atoms. They may be monocyclic or bicyclic. They must contain at least one carbon-carbon double bond in the ring, and may contain more than 1 carbon-carbon double bond in the ring. In an embodiment, they contain up to 3 carbon-carbon double bonds in the ring. Thus the term cycloalkenyl includes cycloalkenyl containing from three to eight ring carbon atoms. They also include cycloalkenyl containing 3, 4, 5, or 6 ring carbon atoms. It may be monocyclic or bicyclic.

The term "cycloalkylalkyl", when used alone or in combination with other groups, refers to alkyl group, as defined hereinabove, substituted with an cycloalkyl group, as defined hereinabove wherein the cycloalkyl group is at the terminal end. Examples include cyclopentylmethyl, cyclohexylethyl, and the like. Similarly, the term "cycloalkenylalkyl", when used alone or in combination with other groups, refers to an alkyl group substituted at the terminal position with cycloalkenyl, as defined herein.

The alkyl, alkylene, alkenyl, alkenylene, alkynyl, alkynylene, cycloalkyl, cycloalkylene, cycloalkenyl, cycloalkenylene, cycloalkylalkyl, cycloalkylenealkylene, cycloalkenylalkyl, cycloalkenylenealkylene and alkoxy groups described hereinabove may be unsubstituted or substituted with one or more substituents selected from alkyl containing 1-6 carbon atoms, hydroxy, halo, including partially or fully halogenated, amino, cyano, nitro, alkoxy containing 1-6 carbon atoms, alky amino, dialkylamino, and the like.

The term "aryl", when used alone or in combination with other groups, refers to an aromatic hydrocarbon containing 6 to 14 ring carbon atoms. It includes aromatic rings fused to non-aromatic rings, as long as one of the fused rings is an aromatic hydrocarbon. Examples include phenyl and naphthyl. It may be unsubstituted or substituted, such as partially or fully halogenated, alkyl, hydroxyl, nitro, —COOH, —CO(lower alkoxy), —COO ower alkyl), amino, alkylamino, dialkylamino, alkoxy, —NCOH, —NCO(lower alkyl), —NSO$_2$-Ph(halo)$_{0-3}$, Phenyl, —O—Ph; naphthyl, —O-naphthyl. In an embodiment, aryl is unsubstituted phenyl or phenyl with at least one of the substituents described hereinabove.

The term "halo" refers to a halogen radical selected from fluoro, chloro, bromo or iodo.

The term "heterocyclic" when used alone or in combination with other groups refers to a 5- to 8-membered (for example, 5- or 6-membered) monocyclic or 8- to 11-membered bicyclic heterocyclic radical which may be either saturated or unsaturated, aromatic or non-aromatic, and which may be optionally benzo- or pyrido-fused if monocyclic, containing at least one ring heteroatom. Each heterocycle consists of carbon atoms and from 1 to 4 ring heteroatoms selected from the group consisting of nitrogen, oxygen and sulfur. As used herein, "nitrogen" and "sulfur" include any oxidized form of nitrogen and sulfur and the quaternized form of any basic nitrogen. Preferred heterocycles include, for example, benzimidazolyl, furazanyl, imidazolyl, imidazolinoyl, quinolyl, isoquinolyl, indolyl, oxazolyl, pyridyl, pyrrolyl, pyrrolinyl, pyrazolyl, pyrazinyl, pyrimidinyl, pyridazinyl, quinoxolyl, piperidmyl, morpholinyl, thiamorpholinyl, furyl, thienyl, triazolyl, thiazolyl, betacarbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofaranyl, thiadiazoyl, benzodioxolyl, tetrahydrothiophenyl and sulfolanyl, and the like. In an embodiment, the heterocycles are imidazolyl, pyridyl, pyrrolyl, pyrazolyl, piperidinyl, morpholinyl, furyl, thienyl, thiazolyl and the benzo- and pyrido-fused derivatives thereof.

"Heterocyclyl" refers to unsubstituted heterocycle radicals as defined hereinabove, those radicals that are partially or fully halogenated and those radicals substituted with alkyl, hydroxyl, nitro, —COOH, —CO(lower alkoxy), —CO(lower alkyl), amino, alkylamino, dialkylamino, alkoxy, —NCO(lower alkyl), —NSO$_2$, -Ph(halo)$_{0-3}$, Ph, —O-Ph, naphthyl, —O-naphthyl, pyrrolyl, pyrrolyl substituted with lower alkyl, pyridyl, pyridinyl, pyrazinyl, pyrimidinyl and pyridazinyl, and the like.

"Alkylene" refers to a linear or branched saturated divalent hydrocarbon radical, which may optionally be substituted as described herein. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_{1-6}$ alkylene refers to a linear saturated divalent hydrocarbon radical of 1 to 6 carbon atoms or a branched saturated divalent hydrocarbon radical of 3 to 6 carbon atoms.

The term "alkenylene" refers to a linear or branched divalent hydrocarbon radical, which contains one or more carbon-carbon double bonds. The alkenylene may be optionally substituted as described herein. Similarly, the term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms, Examples of alkenylene groups include, but are not limited to, ethenylene, allylene, propenylene, butenylene, and 4-methylbutenylene.

The term "alkynylene" refers to a linear or branched divalent hydrocarbon radical, which contains one or more carbon-carbon triple bonds. The alkynylene may be optionally substituted as described herein. The term "alkynylene" also encompasses both linear and branched alkynylene, unless otherwise specified. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene (—C≡C—) and propargylene (—CH$_2$C≡C—). For example, $C_{2-6}$ alkynylene refers to a linear unsaturated divalent hydrocarbon radical of 2 to 6 carbon atoms or a branched unsaturated divalent hydrocarbon radical of 3 to 6 carbon atoms.

The term "cycloalkylene" refers to a cyclic saturated bridged and/or non-bridged divalent hydrocarbon radical, which may be optionally substituted as described herein. In certain embodiments, the cycloalkylene has from 3 to 20 ($C_{3-20}$), from 3 to 15 ($C_{3-15}$), from 3 to 10 ($C_{3-10}$), to), or from 3 to 7 ($C_{3-7}$) carbon atoms. Examples of cycloalkylene groups include, but are not limited to, cyclopropylene (e.g., 1,1-cyclopropylene and 1,2-cyclopropylene), cyclobutylene (e.g., 1,1-cyclobutylene, 1,2-cyclobutylene, or 1,3-cyclobutylene), cyclopentylene e.g., 1,1-cyclopentylene, 1,2-cyclopentylene, or 1,3-cyclopentylene), cyclohexylene (e.g., 1,1-cyclohexylene, 1,2-cyclohexylene, 1,3-cyclohexylene, or 1,4-cyclohexylene), cycloheptylene (e.g., 1,1-cycloheptylene, 1,2-cycloheptylene, 1,3-cycloheptylene, or 1,4-cycloheptylene), decalinylene, and adamantylene.

"Cycloalkenylene" refers to a divalent non-aromatic carbon-based ring composed of at least three carbon atoms and containing at least one carbon-carbon double bond. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples include cyclopropenyl, cyclobutenyl, cyclopentenyl, cyclopentadienyl, cyclohexenyl, cyclohexadienyl, norbornenyl, and the like.

As used herein, "cycloalkylenealkylene" refers to a bivalent moiety, wherein a cycloalkylene group is bonded to a non-cyclic alkylene group, wherein each of the cycloalkylene and non-cyclic alkylene groups has one open bonding site, and wherein cycloalkylene and alkylene are each as previously defined. "Cycloalkylenealkylene" includes moieties having —cycloalkylene-alkylene- and -alkylene-cycloalkylene—bonding orders or configurations.

As used herein, "cycloalkenylenealkylene" refers to a bivalent moiety, wherein a cycloalkenylene group is bonded to a non-cyclic alkylene group, wherein each of the cycloalkenylene and non-cyclic alkylene groups has one open bonding site, and wherein cycloalkenylene and alkylene are each as previously defined. "Cycloalkenylene-alkylene" includes moieties having—cycloalkenylene-alkylene- and -alkylene-cycloalkenylene—bonding orders or configurations.

The term "heterocyclylene" refers to a divalent non-aromatic ring system and/or multicyclic ring system that contain at least one non-aromatic ring, wherein one or more of the non-aromatic ring atoms are heteroatoms independently selected from O, S, or N; and the remaining ring atoms are carbon atoms. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinyiene, dihydropyridinylene, dihydropyrimidinyene, dihydropyrrolyene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinyiene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, heterocyclic may also be optionally substituted as described herein.

The term "heterocyclylenealkylene" refers to a bivalent moiety, wherein a heterocyclylene group is bonded to a non-cyclic alkylene group, wherein each of the heterocyclylene and non-cyclic alkylene groups has one open bonding site, and wherein heterocyclylene and alkylene are each as previously defined. "Heterocyclylene alkylene" includes moieties having -heterocyclylene-alkylene- and -alkylene-heterocyclylene-bonding orders or configurations.

The term "lower", used in conjunction with other terms (e.g., "alkyl", "alkoxy", and the like), refers to a radical containing from one to six, preferably from one to five and more preferably, from one to four carbon atoms. The "lower alkyl" group may be a branched or unbranched alkyl radical containing from one to six carbon atoms.

The phosphate protecting groups are protecting groups for the phosphate groups known in the art. Examples are described in Wuts and Green, "Protective Groups in Organic Synthesis", $4^{th}$ Edition, Wiley-Interscience, 2006, NY, ISBN 978-0471697541, Chapter 9, pg 665-700, the contents of which are incorporated herein by reference. Examples include alkyl phosphates, e.g., methyl, ethyl, 4-(N-trifluoroacetylamino)butyl, isopropyl, cyclohexyl, t-butyl, 1-adamantyl, allyl, 2-trimethylsilylprop-2-enyl, 3-pivaloyloxy-1, 3-dihydroxypropyl, and the like; 2-substituted ethyl phosphates, such as 2-cyanoethyl, 2-cyano-1,1-dimethylethyl, 4-cyano-2-butenyl, $ArNHC(O)CH_2CH_2$— wherein Ar is as defined above, 2-(methyldiphenylsilyl) ethyl, 2-(trimethylsilyl)ethyl, 2-(triphenylsilyl)ethyl, 2-(S-acetythio) ethyl, 2-(4-nitrophenyl)ethyl, 2-(2'-pyridyl)ethyl, 2-(4'-pyridyl)ethyl, 2-(3-arylpyrimidin-2-yl)ethyl, wherein aryl is as defined hereinabove, 2-(phenylthioethyl, 2-(4'-nitrophenyl)thioethyl, 2-'4'-triphenylmethylphenylthio)ethyl, 2-[2'-(monomethoxytrityl(oxy)ethylthio]ethylthio]ethyl, $HOCH_2CH_2SS(CH_2)_2$—, 2-(t-butylsulfonyl)ethyl, 2-(phenylsulfonyl)ethyl, 2-(benzylsulfonyl)ethyl, and the like; haloethyl phosphates, such as 2,2,2-trichloroethyl, 22,2-trichloro-1,1-dimethylethyl, 2,2,2-tribromoethyl, 2,3-dibromopropyl, 2,2,2-trifluoroethyl, 1,1,1,3,3,3-hexafluoro-2-propyl, and the like; benzyl phosphates, including benzyl, o-nitrobenzyl, 4-nitrobenzyl, 2,4-dinitrobenzyl, 4-chlorobenzyl, 4-chloro-2-nitrobenzyl, 4-acyloxybenzyl, 1-oxido-4-methoxy-2-picolyl, fluorenyl-9-methyl, pyrenylmethyl, 2-(9,10-anthraquinolyl)methyl, 5-benzisoxazoylmethylene, diphenylmethyl, o-xylene, benzoin, 3',5'-dimethoxybenzoin, 4-hydroxyphenacyl, 4-methoxyphenacyl, and the like, phenyl phosphates, such as phenyl, 2-methylphenyl, 2-6-dimethylphenyl, 2-chlorophenyl, 4-chlorophenyl, 2,4-dichlorophenyl, 2,5-dichlorophenyl, 2,6-dichlorophenyl, 2-bromophenyl, 4-nitrophenyl, 3,5-nitrophenyl, 4-chloro-2-nitrophenyl, 2-chloro-4-triphenylmethylphenyl, 2-methoxy-5-nitrophenyl, 1,2-phenylene, 4-triphenylmethylaminophenyl, 4-benzylamino-phenyl, 1-methyl-2-(2-hydroxyphenyl)imidazole, 8-quinolyl, 5-chloro-8-quinolyl, thiophenyl, and the like; amidates, such as anilidate, 4-triphenylmethylanilidate, [N-(2-trityloxy)ethyl]anilidate, p-(N,N-dimethylamino)anilidate, p-anisidate, 2,2'-diaminobiphenyl, N,N-dimethyl-(R,R)-1,2-diaminocyclohexyl and morpholinyl and the like.

"Haptens" are partial or incomplete antigens. They are protein-free substances, mostly low molecular weight organic compounds, which are not capable of stimulating antibody formation, but which do react with antibodies. They are formed by coupling the hapten to a high molecular weight immunogenic carrier using conventional conjugate chemistry (as further explained below) and then injecting this coupled product, i.e., immunogen, into a human or animal subject.

The terms "immunogen" and "immunogenic" refer to substances capable of eliciting, producing, or generating an immune response in a living mammal.

The term "conjugate" refers to any substance formed from the joining together of two parts. Representative conjugates in accordance with the present invention include those formed by the joining together of a small molecule, such as the compound of formula I or a hapten of the present invention, as defined hereinabove, and a large molecule, such as a carrier or a polyamino acid or polyamine polymer, particularly a protein. In the conjugate, the small molecule may be joined at one or more active sites on the large molecule, directly or indirectly through a spacer or linking agent. The term conjugate includes the term immunogen.

As used herein, a "spacing group" or "spacer" refers to a portion of a chemical structure which connects two or more substructures such as haptens, carriers, immunogens, labels, or tracers through an alkylene group (i.e., —$CH_2$—) or a functional linking group. The atoms of a spacing group and the atoms of a chain within the spacing group are themselves connected by chemical bonds.

The term "linker" refers to a chemical moiety that connects a hapten to a carrier, immunogen, label, tracer or another linker. Linkers may also be used to attach antibodies to labels or solid substrates. Linkers may be straight or branched, saturated or unsaturated carbon chains. They may also include one or more heteroatoms within the chain or at the termini of the chains. By heteroatoms is meant atoms other than carbon which are chosen from the group consisting of oxygen, nitrogen, sulfur, phosphorus, boron and halogen. The use of a linker may or may not be advantageous or needed, depending on the specific hapten and carrier pairs. Methods and techniques for the attachment of a linker to an antibody are known in the art. For a good treatise on this subject, the reader is referred to Bioconjugate Techniques, G. Hermanson, Academic Press, 1996.

Among the spacers contemplated are straight or branched, saturated or unsaturated, carbon chains. These carbon chains may also include one or more heteroatoms within the chain or at termini of the chains, By "heteroatoms" is meant atoms other than carbon which are chosen from the group consisting of oxygen, nitrogen, sulfur, phosphorus, boron and halogen. Spacing groups may also include cyclic or aromatic groups as part of the chain or as a substitution on one of the atoms in the chain.

The number of atoms in the spacing group is determined by counting the atoms other than hydrogen. More specifically, the number of atoms in a chain within a spacing group is determined by counting the number of atoms other than hydrogen along the shortest route between the substructures being connected. A functional linking group may be used to activate, e.g., provide an available functional site on a hapten or spacing group for synthesizing a conjugate of a hapten with a label or carrier or polyamine polymer. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. Various linking agents are well known in the art; see, for example, Cautrecasas, J. Biol. Chem. 245: 3059 (1970), and Cross-Linking Reagents, Technical Handbook by Pierce Company (Rockford, Ill.)

An "immunogenic carrier," as the term is used herein, is an immunogenic substance, commonly a polypeptide or protein, that can join with a hapten, thereby enabling the hapten to induce an immune response and elicit the production of antibodies that can bind specifically with these haptens. Among the immunogenic carrier substances are included proteins, glycoproteins, complex polyamino-polysaccharides, and nucleic acids that are recognized as foreign and thereby elicit an immunologic response from the host. The polyamino-polysaccharides may be prepared from polysaccharides using any of the conventional means known for this preparation. Also various protein types may be employed as a poly(amino acid) immunogenic carrier. These types include albumins, serum proteins, lipoproteins, and the like. Illustrative proteins include bovine serum albumin (BSA), bovine gamma-globulin (BgG), keyhole limpet hemocyanin (KLH), egg ovalbumin, bovine thyroglobulin (BTG), and the like. A carrier protein solution can be prepared by a number of methods that are outlined in "Bioconjugate Techniques, $2^{nd}$ Edition" by Greg T. Hermanson, Editor (Elsevier Science, 2008). Alternatively, synthetic poly(amino acids), polymerized protein or cross-linked protein may be utilized.

Immunogenic carriers can also include polyamino-polysaccharides, which are high molecular weight polymers built up by repeated condensations of monosaccharides. Examples of polysaccharides are starches, glycogen, cellulose, carbohydrate gums such as gum arabic, agar, and so forth. The polysaccharide also contains poly(amino acid) residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns and not more than about 100 microns, and usually about 0.05 microns to about 10 microns in diameter. The particle can be organic or inorganic, swellable or non-swellable, porous or non-porous, optimally of a density approximating water, generally from about 0.7 to about 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses, and the like. The particles can also be comprised of organic and inorganic polymers, liposomes, latex, phospholipid vesicles, or lipoproteins.

"Poly(amino acid)" or "polypeptide" is a polyimide formed from amino acids. Poly(amino acids) will generally range from about 500 daltons in molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of alpha-amino acids in which the alpha-amino group of each amino acid residue (except the $NH_2$ terminus) is linked to the alpha-carboxyl group of the next residue in a linear chain. The terms peptide, polypeptide and poly(amino acid) are used synonymously herein to refer to this class of compounds without restriction as to size, unless indicated to the contrary. The largest members of this class are referred to as proteins. A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments such as Fab, Fab' and F(ab')$_2$, and the like, and application products containing these materials such as chimeric antibody, or humanized antibody, and the like.

In the present specification, antibody specificity refers to the property of an antibody which enables it to recognize, react, or bind to some particular antigenic determinants and not others. Specificity is dependent on chemical composition, physical forces, and molecular structure at the binding site.

The term "derivative" refers to a chemical compound or molecule made from a parent compound by one or more chemical reactions.

The term "amino acid residue" refers to the amino acid without the hydrogen on the amino group on the amino end and the OH group on the carboxyl at the carboxy end of the amino acid.

The term "carrier" refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to a terminal functional group in the haptens of the present invention.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for immunogens of the present invention, ligands of the analyte and calibration and control materials. The reagents may remain in liquid form or may be lyophilized.

The phrase "calibration and control materials" refers to any standard or reference material containing a known amount of a compound to be measured. The concentration of compound is calculated by comparing the results obtained for the unknown specimen with the results obtained for the standard. This is commonly done by constructing a calibration curve.

"Test sample", as used herein, refers to a sample to be tested. The test sample is typically in liquid form. The test sample is typically a biological sample.

The term "biological sample" includes, but is not limited to, any quantity of a substance from a living organism or formerly living organism. Such living organisms include, but are not limited to, humans, mice, monkeys, rats, rabbits, horses, and other animals, and plants, bacteria, or fungi, and the like. Such substances include, but are not limited to, blood, serum, plasma, urine, cells, organs, tissues, bone, bone marrow, lymph, lymph nodes, synovial tissue, chondrocytes, synovial macrophages, endothelial cells, and skin, and the like.

As used herein, the term "subject" refers to any animal, including, but not limited to, humans and non-human animals (e.g., rodents, arthropods, insects, fish (e.g., zebrafish), non-human primates, ovines, bovines, ruminants, lagomorphs, porcines, caprines, equines, canines, felines, ayes, etc.), which is to be the recipient of a particular treatment. Typically, the terms "patient" and "subject" can be used interchangeably herein in reference to a human subject.

DETAILED DESCRIPTION

The invention provides pyrazole-based synthetic pHis analogs that are useful, inter cilia, as haptens to generate pHis-specific, antibodies. The pHis-specific antibodies can be used to detect and isolate pHis-containing proteins from biological samples. Historically, the advent of phosphotyrosine(pTyr)-specific antibodies in the '80s was pivotal in the explosion of the pTyr research, which eventually led the development of tyrosine kinase inhibitors such as Gleevec® as clinical anticancer drugs. Analogously, potent and selective antibodies towards pHis are expected to open up numerous novel opportunities in basic science and biomedical applications.

The analogs described herein can also be used as inhibitors against protein phosphohistidine phosphatases. Such inhibitors will be, inter cilia, very useful biochemical reagents to elucidate the function of the phosphatase. These inhibitors can be lead compounds for drug discovery.

In one embodiment the invention is directed to pyrazole-based synthetics pHis analogs comprising the following structure:

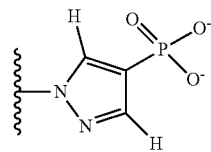

In certain embodiments, the invention is directed to a phosphonopyrazole of formula (I):

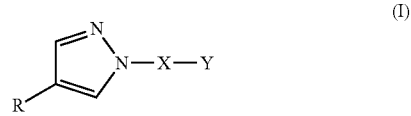

(I)

Wherein
R is

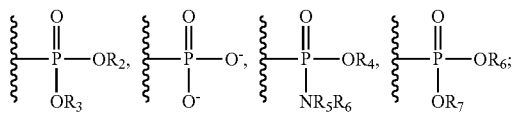

$R_2$, $R_3$, $R_4$, $R_5$, $R_6$, $R_7$, and $R_8$ are each independently alkyl, alkenyl, cycloalkyl, cycloalkylalkyl, aryl, arylalkyl, heterocyclyl, heterocyclylalkyl, or a phosphate protecting group;

X is a chemical bond or a linker group selected from alkylene, alkenylene, alkynylene, cycloalkylene, cycloalkylenealkylene, cycloalkenylene, cycloalkenylenealkylene, heterocyclylene, heterocyclylenealkylene, —(O—CH$_2$—CH$_2$) or —(CH$_2$)$_q$— where one of the —CH$_2$— groups is replaced by —O—;

n is 1-100;
q is 1-6;
Y is H, —OR$_9$, —NR$_9$R$_{10}$, —SR$_9$, —COOR$_9$, —C(O)NR$_9$R$_{10}$, —NHJ or —C(O)Q;
$R_9$ and $R_{10}$ are each independently H, alkyl, alkenyl, alkynyl, cycloalkyl, cycloalkylalkyl, aryl, arylalkyl, heterocyclyl, heterocyclylalkyl;
J is an amino protecting group; and
Q is a carboxylic acid protecting group.
In certain embodiments, R is

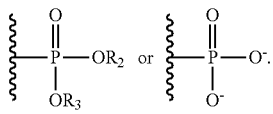

In other embodiments, $R_2$ and $R_3$ are H.
In some embodiments, X is an alkylene linker group. In certain embodiments, X is —CH$_2$—CH$_2$—.
In another embodiment, Y is —NR$_9$R$_{10}$ or —NHJ. In yet another embodiment, Y is —NR$_9$R$_{10}$ and $R_9$ and $R_{10}$ are H.
In certain specific embodiments, R is

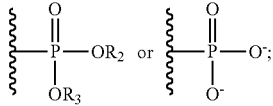

$R_2$ and $R_3$ are H;
X is CH$_2$—CH$_2$—; Y is —NR$_9$R$_{10}$; and $R_9$ and $R_{10}$ are H.
In another embodiment, the phosphonopyrazole of formula I is:

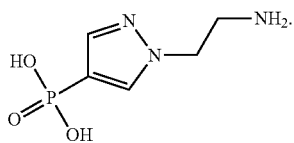 [SMILES: NCCn1cc(P(=O)(O)O)cn1]

In some embodiments, the analogs or phosphonopyrazole compounds of formula I are provided as haptens. The haptens can be prepared using art-recognized techniques.

Another embodiment of the present invention is directed to immunogens in which a hapten of the present invention is coupled to an antibody conferring carrier material. The haptens of the present invention are employed in the preparation of immunogens by coupling them to modified or non-modified antigenicity-conferring carrier materials to provide immunogens for antibody production and conjugates (tracers) using synthetic organic chemistry techniques. The haptens are stable under the conditions used to generate antibodies in a desired host animal, e.g., a rabbit.

The hapten may be bonded directly to the carrier material or indirectly through a linking group. Spacer groups may be added to the hapten or to the carrier. The hapten, on the one hand, may be linked to the carrier by a linker, which links one group on the carrier with another group on the hapten. A hapten can be directly or indirectly (via a spacer or linker) coupled to a carder protein to form an immunogen, such as haptenenzyme conjugate.

The hapten can also be linked to other non-enzymatic reporter groups such as a chromogen, a fluorescent compound, a phosphorescent compound or a chemiluminescent material, and the like. For example, in an embodiment of the present invention, the hapten is a polypeptide wherein the end groups thereon are functional groups, the amino group at one end and a carboxy group at the other end. The linkage may be through the carboxylic acid or phosphoric acid of the hapten and the alcohol if present, on the carrier to form an ester or through the carboxyl group of the hapten and amino group, if present, of the carrier to form an amide bond. However, if necessary, the carboxy group or the amino group may be further functionalized to form other bonds with the carrier molecule. For example, the carboxy group may be reduced to form an alcohol group by techniques known in the art and linked to the carboxyl group, if present, of the carrier to form an ester. Alternatively, the alcohol may be converted to a halide or other good leaving group, such as mesylate, tosylate, brosylate and reacted with other groups on the carrier by substitution reactions. In another embodiment, the side groups of the amino acid residues may react with functional groups on the carrier molecules. For example, a sulfhydryl (mercaptan) can react with an olefin, halogen, or other alkylating agents to form thioethers. In another embodiment, a linking group which contains two functionalities, one reactive with the hapten to be linked thereto and one reactive with the carrier, may be added to either the hapten or the carrier and react with a functional group on the carrier or hapten, respectively, Other bioconjugation reactions can be effected as illustrated in the literature of conjugation chemistry, such as in the Bioconjugate Techniques book described hereinabove. Additionally, if the carrier has a ribose or adenine moiety thereon, it can be coupled to the haptens of the present invention via the functional groups in the ribose or the adenine moiety.

The carrier material typically is a protein, a protein fragment, a synthetic polypeptide or a semi-synthetic polypeptide. Illustrative examples of useful carrier materials are bovine serum albumin (BSA), egg ovalbumin, bovine gamma globulin, thyroxine binding globulin, keyhole limpet haemocyanin (KLH) and the like. Alternatively, synthetic poly(amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen.

Each hapten of the present invention can also be coupled to a labeling agent. For example, it may be coupled to an enzyme. Any common reporter enzyme (e.g., alkaline phosphatase or AP, and beta-galactosidase or beta-gal, horseradish peroxidase or HRP, and the like) can be use for preparation of hapten-enzyme conjugate. The hapten may be coupled to a substance having fluorescent properties or a radioactive label for the preparation of conjugates (or detection reagents) for use in the immunoassay. The fluorescent substance may be, for example, a monovalent residue or fluorescein or a derivative thereof.

In order to confirm that adequate conjugation of hapten to carrier material has been achieved prior to immunization, each immunogen is evaluated to verify that the hapten is conjugated to a carrier material. For example, the immunogen may be evaluated using matrix-assisted UV laser desorption ionization time of flight mass spectroscopy (MALDI-TOF-MS).

The immunogens obtained are then administered to hosts to elicit production of specific antibodies, i.e., polyclonal or monoclonal antibodies, which are then used to develop immunoassays for the detection and determination of p-His polypeptides in a biological sample. Each of the immunogens of the present invention is suitable for immunization to produce the antibodies described hereinbelow. For specific application, the hapten may be coupled to antibody, or biotin/avidin (or streptavidin), and the like.

The immunogen is administered to animals such as rabbits, mice, rats, chickens, sheep, goats, or cows, and the like by a series of injections according to techniques generally known in the art. An antibody, according to the present invention, is raised in response to an immunogen of the invention which is derived from a substantially purified hapten including optically pure hapten of the invention.

The present invention is also directed to processes of preparing antibodies to the immunogens described above, comprising
 (a) immunizing an animal by administering an immunogen comprising a hapten comprised of the phosphonopyrazole of formula I, said hapten conjugated to an antigenicity-conferring carrier material;
 (b) collecting the resulting serum from the immunized animal;
 (c) detecting the antibodies which recognize a phosphorylated polypeptide, wherein at least one histidine residue thereon is phosphorylated; and
 (d) isolating said antibody therefrom.

In certain embodiments, administration of the immunogen to the animal is repeated 1-5 times.

The antibodies generated by this process will not recognize a polypeptide which is not phosphorylated or which is phosphorylated on an amino acid other than histidine.

Both polyclonal and monoclonal antibodies recognize specific epitopes on an immunogen, and, while typically polyclonal antibodies have been utilized in the present invention, both may be suitable. Polyclonal antibodies consist of a mixture of multiple antibodies, each recognizing a specific epitope, whereas monoclonal antibodies are produced by cells secreting a single antibody recognizing a specific epitope. Techniques for preparing polyclonal antibodies and monoclonal antibodies generally are well known in the art.

Thus, the specific antibodies of the present invention will recognize phosphopolypeptides which contain at least one phosphorylated histidine. The antibodies do not recognize amino acids other than histidine which are phosphorylated, nor do they recognize peptides including polypeptides, which are not phosphorylated or are phosphorylated on amino acids other than histidine. As long as the peptide contains one histidine moiety that is phosphorylated, even if the other histidine moieties therein are not phosphorylated, the antibody will recognize the peptide.

Thus, even after separation of the antibodies, and the antibodies are isolated, to verify that the correct antibodies are collected non-phosphorylated histidine or a peptide containing non-phosphorylated histidine is used. If the antibody does not recognize the non-phosphorylated histidine, then the antibody is kept. If the antibody still recognizes the dephosphorylated His or peptide containing non-phosphorylated histidine, then the antibody is discarded.

In some embodiments, the anti-phosphohistidine antibodies described herein bind with at least 2-fold greater affinity to a phospho-His substrate compared to its binding affinity for the corresponding non-phospho-His substrate. In certain embodiments, the anti-phosphohistidine antibodies bind with at least 5-fold, 10-fold, 15-fold, or 20-fold greater affinity to a phospho-His substrate compared to its binding affinity for the corresponding non-phospho-His substrate.

In some embodiments, the antibodies bind with at least 2-fold greater specificity for a phospho-His substrate than for a phospho-Tyr substrate. In certain embodiments, the anti-phosphohistidine antibodies bind with at least 5-fold, 10-fold, 15-fold, or 20-fold greater specificity for a phospho-His substrate than for a phospho-Tyr substrate.

Accordingly, the invention includes methods for detecting phosphopolypeptides containing at least one phosphorylated histidine in a biological sample comprising:
 (a) providing the antibody generated as described herein;
 (b) contacting a biological sample suspected of containing phosphorylated histidine with said antibody under conditions suitable for formation of a complex between said antibody and said phosphorylated polypeptide; and
 (c) detecting the presence of the complex the sample, where the presence of the complex indicates the presence of phosphorylated polypeptides where at least one histidine residue is phosphorylated.

The polyclonal antibodies are obtained by techniques known in the art. For example, in a method to generate anti-sera and polyclonal antibodies, each immunogen is mixed with Freud's Adjuvant and the mixture injected into a host animal, such as rabbit, sheep, mouse, guinea pig or horse. Further, injections (boosts) are made and their serum is sampled for evaluation of the antibody titre. When the optimal titre has been attained, the host animal is bled to yield a suitable volume of specific anti serum. For many purposes, there is no requirement for purification, however, in other cases, such as where the antibody is immobilized on a solid support, purification steps can be taken to remove undesired material. The antibodies are then separated from the serum using techniques known in the art.

For example, monoclonal antibodies may be prepared by injecting animals, such as mice or rats, intraperitoneally, subcutaneously, intravenously, or in some other manner, with an antigen, namely an immunogen of the present invention linked to an immunogenic carrier, to elicit an immune response in the animals (namely, the production of antibodies which are specific for the antigen). Sera from the animals are drawn, and the sera are tested to determine the titer of antibody in the sera (to determine whether or not the animal elicited the desired immune response, and to what extent). Those animals in which the desired immune response has been produced are permitted to rest for approximately three weeks to three months for clearance of circulating antibodies. After this three weeks to three-month period of time, and approximately three days prior to the anticipated fusion of B-lymphocyte cells (cells which, upon stimulation by antigen, mature into plasma cells which synthesize antibody, and which are also referred to as B cells) with, for example, myeloma cells (tumor cells), a boost injection (intravenously preferred) of the antigen is administered to these animals. B-lymphocyte cells are then removed from the spleens and/or lymph nodes of these animals by standard procedures, and the B-lymphocyte cells are then fused with myeloma fusion partners according to standard procedures, such as those described in Ed Harlow and David Lane, "Antibodies, A Laboratory Manual," Cold Spring Harbor Laboratory, 1988, and in Kohler and Milstein, "Continuous Culture of Fused Cells Secreting Antibody of Predefined Specificity," Nature, 256, 495 (1975). The B-lymphocyte-myeloma fusions are then plated in multiwell tissue culture plates containing HT media, or other suitable media. The resulting cultures are fed with HT media, or other suitable media, and fetal bovine serum or calf serum on or about the fifth and seventh days after the fusion of the cells and then tested on or about the tenth day after the fusion for the presence of antibody which is specific for the antigen. Specific desirable hybrids are then cloned by limiting dilution. (Hybrid cells are diluted in differing amounts of HT media, or other suitable media, and plated out in tissue culture plates in order to isolate a single desired clone.) Established clones are then retested for specificity to a broader panel of cross reactants.

The amount of the resulting monoclonal antibodies produced by a desired clone can then be scaled up to produce a sufficient quantity of antibody for purification in either: (1) tissue culture (by expanding the number of cells in tissue culture, or media); or (2) mice for ascites. The monoclonal antibodies can be scaled up in mice by injecting hybrid cells into the abdominal cavity of mice and allowing the cells to grow (usually for about 7 days).

The ascites are harvested from the mice by sacrificing the mice, collecting the ascites fluid, and purifying the ascites fluid. BALB/c mice are the most common strain of laboratory mouse used for this process, and they can be obtained from any mouse vendor. Pristane should be injected into the mice to stimulate their immune systems to produce B and T cells (about two or three weeks before the hybrid cells are injected into the mice) which serve as a feeder layer for the clone cells that are injected into the mice. This is performed to provide a suitable environment in which the hybrid cells can grow.

The antibody fragments comprise a portion of an intact antibody, generally the antigen binding or variable region of the intact antibody. Examples of antibody fragments include Fab, Fab', F(ab')$_2$, Fv and Fc fragments; diabodies; linear antibodies; single-chain antibody molecules; and multispecific antibodies formed from antibody fragments.

The antibody application derivatives and products are intended to include chimeric antibodies, humanized antibodies, genetically engineered or modified antibody sequences by site-specific mutagenesis.

An additional method for selecting antibodies that specifically bind to the immunogens of the present invention or variant or fragment thereof is by phage display. In an embodiment, the antibodies prepared by the techniques hereinabove are collected. In one embodiment, a process for isolating an antibody comprises:
   (a) exposing the immunogen of the present invention to a phage display library expressing antibodies;
   (b) isolating the phages and antibodies that bind to the immunogen; and
   (c) collecting the antibodies that bind to phosphorylated histidine in a polypeptide but not to a non-phosphorylated peptide or a peptide containing phosphorylation on an amino acid other than histidine.

Human or murine immunoglobulin variable region gene combinatorial libraries may be created in phage vectors, that can be screened to select the antibodies fragment (Fab, Fb, sFv or multimers thereof) that bind specifically to the immunogen of the present invention or variants or fragments thereof, but do not bind to the corresponding non-phosphorylated polypeptide using phase transfer techniques known to one of ordinary skill in the art. For example, a library containing a plurality of polynucleotide sequences encoding the antibody isolated hereinabove or variable region fragments can be prepared and inserted into the genome of a filamentous bacteriophage, such as M13 or variant thereof, in frame, with the sequence encoding a phage coat protein, for instance, gene III or gene VIII of M13 to create an M13 fusion protein with the antigen binding domain on the outside of the bacteriophage. The fusion protein may be a fusion of the coat protein with the light chain variable region domain and/or with the heavy chain variable region domain. A random population of variable region genes are cloned to give rise to a mixture of bacteriophages, that is a phase display library.

Phage that display an Ig fragment (e.g., an Ig V-region or Fab) that binds to the immunogen of the present invention may be selected by mixing the phage library with the immunogen of the present invention or a variant or a fragment thereof, or by contacting the phage library with a immunogen of the present invention immobilized on a solid matrix under conditions and for a time sufficient to allow binding. Unbound phage are removed by a wash, which typically may be a buffer containing salt (e.g., NaCl) at a low concentration, preferably with less than 100 mM NaCl, more preferably with less than 50 mM NaCl, most preferably with less than 10 mM NaCl, or, alternatively, a buffer containing no salt.

Specifically bound phage is then eluted with a NaCl-containing buffer, for example, by increasing the salt concentration in a step-wise manner. Typically, phage that bind the immunogen of the present invention with higher affinity will require higher salt concentrations to be released. Eluted phage may be propagated in an appropriate bacterial host, and generally, successive rounds of immunogen of the present invention binding and elution can be repeated to increase the yield of phage expressing immunogen of the present invention specific immunoglobulin.

Phage display techniques may also be used to select polypeptides, peptides or single chain antibodies that bind to immunogen of the present invention. The inserted DNA molecules may comprise randomly generated sequences, or may encode variants of a known peptide or polypeptide domain that specifically binds to the immunogen of the present invention, or variant or fragment thereof, as provided herein. Generally, the nucleic acid insert encodes a peptide of up to 60 amino acids, more preferably a peptide of 3 to 35 amino acids, and still more preferably a peptide of 6 to 20 amino acids. The peptide encoded by the inserted sequence is displayed on the surface of the bacteriophage. Phage expressing a binding domain for the immunogen of the present invention may be selected on the basis of specific binding to an immobilized immunogen of the present invention as described above. As provided herein, well-known recombinant genetic techniques may be used to construct fusion proteins containing the fragment thereof. For example, a polypeptide may be generated that comprises a tandem array of two or more similar or dissimilar affinity selected immunogens of the present invention binding peptide domains, in order to maximize binding affinity for the immunogen of the present invention of the resulting product.

In certain other embodiments, the invention contemplates the specific antibodies to the immunogens of the present invention that are multimeric antibody fragments. Useful methodologies are described generally, for example in Hayden et al., 1997, Curr. Opin. Immunol. 9:201-12; Coloma et al., 1997, Nat. Biotechnol. 15:159-63. For example, multimeric antibody fragments may be created by phage techniques to form miniantibodies (U.S. Pat. No. 5,910,573) or diabodies (Holliger et al., 1997, Cancer Immunol. Immunother. 45: 128-130), Multimeric fragments may be generated that are multimers of Fv region of the immunogen of the present invention, or that are bispecific antibodies comprising the immunogen of the present invention or specific Fv region of the immunogen of the present invention noncovalently associated with a second Fv having a different antigen specificity. See, e.g., Koelemij et al., 1999, J. Immunother. 22:514-24. As another example, a multimeric antibody may comprise a bispecific antibody having two single chain antibodies or Fab fragments. According to certain related embodiments, a first Ig fragment may be specific for a first antigenic determinant on an immunogen of the present invention (or variant or fragment thereof), while a second Ig fragment may be specific for a second antigenic determinant of an immunogen of the present invention. Alternatively, in certain other related embodiments, a first immunoglobulin fragment may be specific for an antigenic determinant of the immunogen of the present invention or variant or fragment thereof, and a second immunoglobulin fragment may be specific for an antigenic determinant on a second unrelated molecule. Also contemplated are bispecific antibodies that specifically bind, wherein at least one antigen-binding domain is present as a fusion protein.

The invention also provides an immunoassay for determining the presence or amount of phosphorylated histidine polypeptide in biological samples. The immunoassay of the invention includes a step of contacting the biological sample to be determined with antibodies raised in response to an immunogen of the invention. It is contemplated that any immunoassay for peptides containing at least one phosphorylated histidine utilizing haptens, immunogens, and/or antibodies raised against immunogens, are within the scope of the present invention. Examples of immunoassays include radioimmunoassays (RIAs), enzyme immunoassay (EIAs), enzyme-linked-immunosorbent assays (ELISAs) and fluorescent polarization immunoassays (FPIAs), etc. Comprehensive reviews on immunoassay principles, critical components, and assay designs can be readily found in literature. One example is "The Immunoassay Handbook, 3 Edition" by David Wild, Editor (Elservier Science, 2005), another is "Immunoassay," E. P. Diamandis and T. K. Christopoulos, Editors, Academic Press, Inc., 1996.

The immunoassays of the invention may be heterogeneous or homogenous. In heterogeneous assays, the purpose of the label is simply to establish the location of the molecule to which it is conjugated i.e., to establish whether the labeled molecule is free in solution or is part of a bound complex. Heterogeneous assays generally function by explicitly separating bound antigen-antibody complexes from the remaining free antigen and/or antibody. A method frequently employed consists of attaching an antigen or antibody to a solid surface by covalent bonding, physical absorption or some other means. When antigen-antibody binding occurs, the resulting bound complexes remain attached to the solid surface which is composed of any suitably inert material such as plastic, paper, glass, metal, polymer gel and the like. This allows for separation of free antigen and/or antibody in the surrounding solution by a wash step. A variation of this method consists of using small (typically 0.05 to 20 microns) suspendable particles to provide the solid surface onto which either antibody or antigen is immobilized. Separation is effected by centrifugation of the mixture of sample, reagents and suspendable beads at an appropriate speed, resulting in selective sedimentation of the support particles together with the bound complexes. Alternative solid capture phases, such as magnetic particles, glass beads, plastic tubes, glass wool, latex beads, and the like may also be used.

The capture mechanism may be simply by binding to immobilized secondary antibody or an antigen or to utilize, for example, avidin/streptavidin-biotin type of binding pairs. Natural or man-made binding pairs can be adapted to capture the signals from the rest of the assay mixture.

Signal reporting can be by UV or visible light, fluorescence, luminescence, photon, gold sol, and chemiluminescence, and the like. Furthermore, application of such an antibody includes assay variation which utilizes latex beads, liposome, vesicles, and the like to carry signals or signal precursors, and utilize channeling processes, PCR or similar methods to amplify signals. Furthermore, assay formats that are semi-heterogeneous or quasi-heterogeneous (e.g. Roche's Elecsys® assay), can also be applied to the assays of the invention.

Use of an enzyme as a label has produced a variety of useful enzyme immunoassays (EIA), the most popular of which is known as ELISA. For a review, see "Enzyme Immunoassay (EIA)/Enzyme-Linked Immunosorbant Assay (ELISA)" by Rudolf M. Lequin, Clinical Chemistry, 51: 2415-2418, 2005. In one typical heterogeneous format a competition reaction is employed, in which the ligand of interest, a p-His polypeptide, binds to the specific antibody-enzyme conjugate. After suitable incubation, any remaining free enzyme conjugate is eliminated by washing or other separation methods. A suitable substrate for the enzyme is then brought into contact with the surface containing the bound complexes. The enzyme-substrate pair is chosen to provide a reaction product which yields a readily detectable signal, such as a color change or a fluorescence emission. The use of an enzyme as a label serves to effectively amplify the contribution of a single labeled bound complex to the measured signal, because many substrate molecules can be converted by a single enzyme molecule.

In another type of assay, an enzyme is covalently coupled to avidin/streptavidin and the resulting enzyme labeled avidin/strepavidin is then mixed or combined with biotin-labeled reagent (i.e., biotin-labeled ligand or biotin-labeled specific binding substance for said ligand) prior to or during utilization of the latter in a specific binding reaction. The basic components in the binding reaction are, in addition to the biotin-labeled reagent, liquid medium or sample (presumed to contain the ligand to be detected) and an insoluble phase containing a specific binding substance for said ligand. The biotin-labeled reagent may be bound to enzyme labeled avidin/streptavidin after it has been mixed or combined with the insoluble phase or, alternatively, the biotin labeled reagent may be pre-combined with enzyme labeled avidin and the resulting conjugate used directly.

Following the specific binding reaction, the enzyme activity of either the insoluble phase or the liquid phase is determined by a suitable detection system; the amount of activity being related to the quantity of ligand in the sample.

For immunoassays with no separation of bound vs. unbound species (homogeneous assays), Enzyme-Mediated Immunoassay (EMIT) exemplifies such an approach, Based on the functional change of an enzyme such as glucose-6-phoshate dehydrogenase, or G6PDH (commonly shown in diminishing activity) of the hapten-enzyme conjugate when bound to the specific antibody, the assay is achieved by contacting sample with an appropriate amounts of antibody and hapten-enzyme conjugate. When there is a large quantity of analyte in the sample, few of the hapten-enzyme conjugates are bound to the antibody (i.e., minimal amount of enzyme activity is attenuated) and the assay mixture exhibits maximal enzyme activity turning over maximal amount of substrate NAD (or NADP) to NADH (or NADPH). By contrast, when there is little analyte present, the majority of the hapten-enzyme conjugates are bound to antibody, and the assay mixture thus reports substantially reduced signal due to diminished enzyme activity.

Thus, the antibodies are selected and characterized for specificity using standard techniques known in the art, such as standard affinity chromatography, dot blot and ELISA assay protocol. The antibodies isolated by these techniques recognize the pHis polypeptide but not free histidine or other phosphoamino acids.

More specifically, the antibodies of the present invention recognize the immunogens of the present invention. In addition, the antibodies will recognize a phosphorylated histidine, e.g., polypeptides which have at least one phosphorylated histidine thereon, but will not recognize a non-phosphorylated polypeptide or amino acid or a polypeptide in which the phosphorylation is present on amino acids other than histidine and not on any of the histidines present.

In an embodiment, immunogens of various polypeptides are prepared by linking carrier molecules such as KLH through reactive cysteine sulfhydryl group to the polypeptides, and then injecting the resulting product into host animals such as rabbits. Then the antibodies are collected and isolated in accordance with techniques known in the art. The sera are screened for antibodies that recognize phosphorylated histidine and polypeptides which have a phosphorylated histidine, but will preferably not recognize a non-phosphorylated polypeptide or amino acid or a polypeptide which is phosphorylated on an amino acid other than histidine.

Another aspect of the present invention is directed to a kit for detecting and determining p-His polypeptides in a sample. The kit includes the hapten, which may or may not be immobilized and the antibodies of the present invention or a mixture thereof. The kit may optionally include instruction for use of the haptens and the antibodies for detecting and/or determining the presence of phosphorylated polypeptides comprised of at least one phosphorylated histidine residue.

In a specific embodiment, the present invention is a kit for determining histidine phosphorylation status in a cell sample, the kit comprising a container and the antibody of the present invention. In some embodiments, the antibody is fused or conjugated to a detectable label. In other embodiments, the kit further comprises a solution comprising a labeled secondary antibody or a solution comprising a labeled antigen, a washing solution, and a reagent solution comprising a substrate.

The preparation of various antibodies by the procedure described opens the door to perform numerous investigations, such as investigation the mechanism of action of the phosphorylation reactions and dephosphorylation reactions. The haptens, when linked to carrier molecules, generate immunogens, and when administered to a host, generate antibodies, which are isolated from the sera thereof. These antibodies are used to study the mechanism of the phosphorylation and dephosphorylation reactions at the molecular level. For example, the p-His antibodies can be used to follow the biochemical enrichment of the histone histidine kinase in nuclear lysates from cultured cells. Extracts derived from regenerating rat liver cells and Walker-256 carcinosarcoma cells, where high histone histidine kinase (HHK) activity has been observed, can be utilized. The nuclei is isolated from cells and the soluble nuclear proteins separated from the chromatin pellet with KCl extraction. The HHK activity in each fraction is evaluated by utilizing the antibodies.

Further fractionation is effected using hydroxy apatite chromatography of the solubilized pellet and weak ion exchange chromatography of the soluble nuclear proteins. As the activity is enriched, mass spectrometry is utilized to identify the proteins in the active fraction. Candidates, in particular those predicted or known to bind ATP, can be generated by recombinant expression in a host animal and assayed for HHK activity in the reconstituted assay with H4.

In another embodiment, the present invention is directed to assessing whether a patient has liver cancer or tendency to contract liver cancer. Liver cancer is the third most common cancer in the world. Quite often the diagnosis of liver cancer is too late. As indicated hereinabove, the histone H4 histidine kinase activity is upregulated by 200-fold in human hepatocellular carcinomas compared to normal liver tissue. Thus, there is an abnormal level of phosphorylation of histones if a patient has liver cancer. Since the H4 sequence is highly conserved from yeast to man and is, in fact, invariant around the two histidines at positions 18 and 75, one can utilize the antibodies of the present invention to determine if a patient has liver cancer prior to its manifestation. This is determined by contacting a biological sample such as sera or tissue lysate of a patient suspected of having liver cancer with an antibody of the present invention using any of the immunoassays described hereinabove under conditions sufficient for formation of a complex between the antibody and a phosphopolypeptide in the biological sample in which the histidine is phosphorylated, detecting the presence and determining the concentration of the phosphopolypeptide in the sera and comparing the concentration to normal levels of phosphopolypeptide in the sera, whereupon a significantly enhanced concentration of said complex, e.g., above about 100 times relative to the normal concentration, would indicate that the patient has liver cancer or is at a high risk for liver cancer and treatment can be started early.

In another embodiment, the present invention relates to methods of assessing virulence of a microbial infection in a subject, comprising contacting a sample from a subject suspected of having a microbial infection with the anti-phosphoHis antibody under conditions that allow for specific binding between the antibody and a phosphoHis-containing protein; and detecting the specific binding, where increased amounts of specific binding in the sample compared to amounts of binding in a control sample from a subject known not having a virulent infection indicates the infection is virulent.

In some embodiments, the infection is a *Staphylococcus* infection. In one embodiment, the phosphoHis-containing protein is AgrC, and the phosphorylation of AgrC is assessed.

In another embodiment, the infection is a Pseudomonas aeruginosa infection. In one embodiment, phosphorylation of KinB is assessed.

Also contemplated are methods of determining whether a bacterial population is a biofilm-forming population, comprising contacting a test sample of the bacterial population with the anti-phosphol-His-antibody under conditions that allow for specific binding between the antibody and a phosphoHis-containing protein; and detecting the specific binding.

A binding pattern in the test sample similar to binding in a reference biofilm-forming population of the same bacteria indicates the bacteria population is a biofilm-forming population.

The invention will be further illustrated in the following non-limiting examples.

Example 1

Synthesis of a Phosphonopyrazole Analog (pPye)

A synthesis of pPye is shown below:

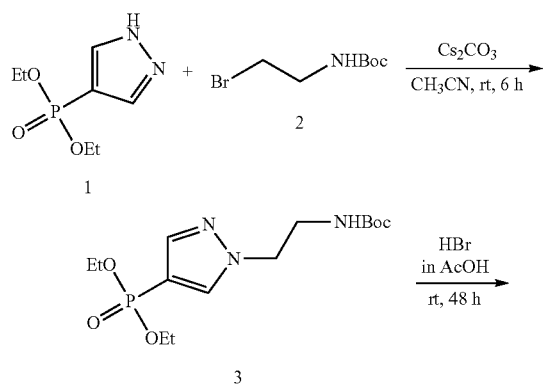

Synthesis of Compound 1

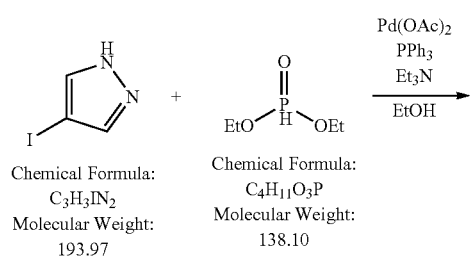

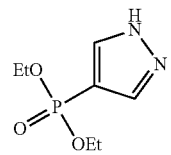

Chemical Formula: $C_7H_{13}N_2O_3P$
Molecular Weight: 204.16

In a 250 mL round bottom flask connected with a reflux condenser, 4-iodopyrazole (2.9 g, 15 mmol), diethyl phosphite (3.86 mL, 30 mmol), PPh$_3$ (1.6 g. 6 mmol), Et$_3$N (4.1 ml. 30 mmol) were dissolved in 100 mL EtOH under argon atmosphere. The solution was heated to 60° C. Pd(OAc) (336 mg, 1.5 mmol) was added in one portion, and the atmosphere flushed with argon. The reaction mixture was refluxed overnight under argon atmosphere for 15 hours, then quenched with 100 mL of NH$_4$Cl (aq. phase pH~7) and extracted with EtOAc (4×100 mL), Some hexane was added to facilitate the phase separation.

The combined organic phases were washed with brine and evaporated under reduced pressure. The resulting yellow residue was loaded onto a silica gel column (5 cm×25 cm, packed with EtOAc) and eluted with 100% EtOAc. The collected product fractions were evaporated to afford compound 1 as a white solid (870 mg, 28% yield).

$^1$H NMR (501 MHz, CDCl$_3$) δ12.06 (s, 1H, pyrazole N—H), 7.85 (d, 2H, pyrazole C—H), 4.03 (m, 4H, P(OCH$_2$CH$_3$)$_2$), 1.25 (t, 6H, P(OCH$_2$CH$_3$)$_2$) ppm.

$^{13}$CNMR (126 MHz, CDCl$_3$): δ138.21 (pyrazole aromatic), 106.28 (pyrazole C-P), 77.09 (P(OCH$_2$CH$_3$)$_2$) 16.32 (P(OCH$_2$CH$_3$)$_2$) ppm.

$^{31}$P NMR (200 MHz, CDCl$_3$): δ15.10 ppm.

Synthesis of Compound 3

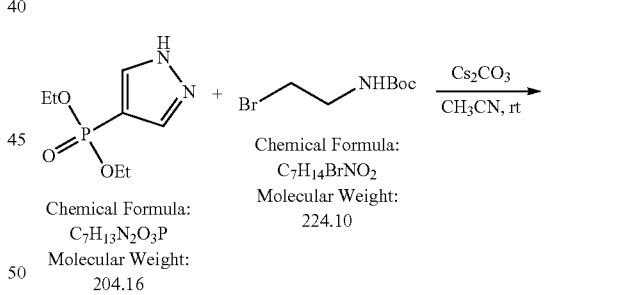

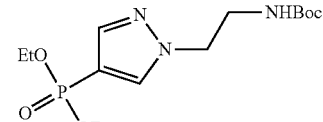

Chemical Formula: $C_{14}H_{26}N_3O_5P$
Molecular Weight: 347.35

In a round bottom flask equipped with a magnetic stir bar, compound 1 (105 mg, 0.51 mmol) and 2-(Boc-amino)ethyl bromide (160 mg, 0.72 mmol, compound 2) were dissolved in 2 mL of acetonitrile at room temperature under argon atmosphere. Cesium carbonate (590 mg, 1.80 mmol) was added to the reaction mixture in one portion, and the mixture stirred vigorously at room temperature under argon for 4 h.

The reaction mixture was diluted with EtOAc (5 mL) and filtered to remove any solids. The resulting solution was evaporated under reduced pressure and the crude product was purified by silica gel flash column chromatography (100% EtOAc) to obtain 150 mg of compound 3 as a colorless oil (yield=71%).

$^1$H NMR (501 MHz, CDCl$_3$) δ7.70 (s, 2H, pyrazole CH), 4.87 (s, 1H, NHBoc), 4.21 (t, J=5.5 Hz, 2H, alkyl CH$_2$), 4.12-3.91 (m, 4H, P—OCH$_2$CH$_3$x2), 3.60-3.43 (m, 2H, alkyl CH$_2$), 1.37 (s, 9H, tell-butyl), 1.26 (t, J=7.1 Hz, 6H, P—OCH$_2$CH$_3$x2) ppm.

$^{13}$C NMR (126 MHZ, CDCl$_3$) δ155.8, 142.8, 135.3, 108.6, 79.9, 62.1, 51.9, 40.4, 28.3, 16.3 ppm.

$^{31}$P NMR (200 MHz, CDCl$_3$) δ13.66 ppm.

Synthesis of Compound 4

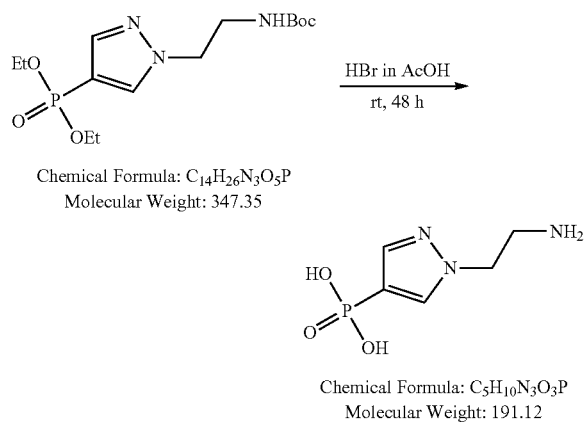

In a round bottom flask equipped with a magnetic stir bar, compound 3 (1.08 g, 3 mmol) was charged, and one portion of HBr (33% in acetic acid, 12 ml, 0.25M) was added to the flask at room temperature. The flask was flushed with argon and the reaction mixture was stirred at room temperature for 2 days.

The reaction mixture was concentrated using a rotary evaporator to afford a solid residue, which was purified on a silica gel column (pre-conditioned with EtOH:water:ammonium hydroxide, 5:3:1). Combined product fractions (~400 mL) were concentrated to a minimal volume (~50 mL) using a rotary evaporator and lyophilized to afford compound 4 as a white amorphous solid. 415 mg (yield=67%).

$^1$H NMR (501 MHz, D$_2$O) δ7.70 (d, J=2.2 Hz, 1H, pyrazole CH), 7.52 (d, J=1.5 Hz, 1H, pyrazole CH), 4.31 (t, J=5.6 Hz, 2H, alkyl CH$_2$), 3.31 (t, J=5.6 Hz, 2H, alkyl CH$_2$) ppm.

$^{13}$C NMR (126 MHz, D$_2$O) δ142.4 (d, J=12.6 Hz), 133.9 (d, 19.8 Hz), 48.1, 39.1 ppm.

$^{31}$P NMR (200 MHz, CDCl$_3$) ░░░ 5.26 ppm.

HRMS: observed [M+H]$^+$=192.0531, m/z=191.04583, predicted for C$_5$H$_{10}$N$_3$O$_3$P=191.04598 (error 0.79 ppm).

The second pKa for the pPye intermediate showed a $^{31}$P shift at about 6.7, which is similar to the corresponding pKa for pHis. This means that both the pPye and pHis have the same charge state at physiological pH. Since the pKa2 of pHis is ~3, both of the phosphate group oxygen atoms in pHis will be deprotonated. For pPye, the doubly deprotonated state will be favored at physiological pH (pH 7.4), well mimicking pHis.

Example 2

Conjugation of Phosphonopyrazole Analog to a Carrier Protein and Generation of Anti-Phosphohistidine Anti-Sera Anti-sera to a phosphonopyrazole analog were generated using a prime-boost protocol by covalent attachment of the phosphonopyrazole analog to a carrier protein using glutaraldehyde.

KLH was dissolved in 500 µl of 0.1 M sodium borate (pH 7-10) at 1-10 mg/ml. This solution was then added to a solution of the phosphonopyrazole analog pPye (3-5 mgs dissolved in 500 µl 0.1 M sodium borate buffer). Glutaraldehyde (1% w/w) final concentration was added, and the mixture was stirred at room temperature for 1 hour. The reaction was quenched by the addition of 50 µl of 1 M Tris, diluted with PBS, and directly injected into rabbits for the production of anti-sera.

As an alternative to the above procedure, after incubation with glutaraldehyde, the imine formed during the cross-linking reaction can be reduced by NaBH$_3$CN or NaBH$_4$, and then either dialyzed into PBS or purified by gel-filtration. The sample can then be injected into rabbits for the production of anti-sera.

Example 3

Affinity Purification of Anti-Phosphohistidine Polyclonal

An affinity resin of phosphorylated BSA immobilized onto agarose was prepared by covalently attaching BSA to agarose beads using SulfoLink Resin according to the manufacturer's instructions. Chemical phosphorylation of the immobilized BSA-agarose resin was performed by pre-equilibrating 1 mL of resin in TBS followed by incubation of the resin in 500 mil potassium phosphoramidate in TBS overnight at room temperature with mixing on a nutator [Tris Buffered Saline (TBS): 25 mM Tris pH 8.5, 137 mM NaCl, 2.7 mM KCl]

The resin was then washed with 4 column volumes of TBS. Crude polyclonal pHis antiserum (600 µl) diluted 5-fold into TBS was then added to the resin and incubated for 1 hour at room temperature on a nutator mixer. The flow through was collected and the resin was washed with 6 column volumes of TBS. Antibodies were eluted from the column in 1 mL fractions with elution buffer Elution Buffer: Elution Buffer: 100 mM Glycine pH 2.5)

After elution from the column, the elution fractions were immediately neutralized by adding 100 µL of 1 M Tris (pH 8.0). Fractions containing pHis antibody (determined by ELISA, see below) were pooled together, and the concentration of antibody was determined by measuring the A$_{280}$ (A$_{280}$ extinction coefficient assumed to be 14 for a 10 mg/ml antibody solution).

ELISA of Affinity Purification Fractions
Buffers Used in ELISA Protocol
  Coating Buffer: 0.032 M Na$_2$CO$_3$, 0.068 M NaHCO$_3$, pH 9.6
  Wash Buffer: 25 mM Tris pH 8.5, 137 mM NaCl, 2.7 mM KCl, 0.1% v/v Tween 20.

BSA and BSA-pHis in 1 mg/ml, stock solutions were diluted 10-fold into coating buffer and 50 µL of each sample was added to a Nunc-Immuno Maxisorp 96-well plate to give 5 µg protein/well. The plate was incubated for 2 hours at room temperature on a nutator mixer. The wells were then washed three times with wash buffer. The wells were then blocked by adding 1% BSA in wash buffer at 50 µL/well and incubating for 45 minutes at room temperature on a nutator mixer. The blocking solution was then removed from each well. The input, flow through, wash, and elution fractions from the antibody purification were each diluted 200-fold into wash buffer and then added to the wells at 50 µL/well and incubated for 45 minutes at room temperature on a nutator mixer. The wells were then emptied, and washed three times with wash buffer. Goat-anti rabbit-HRP secondary antibody was diluted 5000-fold into wash buffer, added to the wells at 50 µL/well, and incubated for 45 minutes at room temperature on a nutator mixer. The wells were emptied and washed four times with wash buffer, Ultra. TMB ELISA substrate (50 µL) was added to each well and incubated for 5 minutes at room temperature, followed by addition of 50 µL of 2 N $H_2SO_4$ to quench the reaction. The absorbance at 450 nm was measured on a Spectramax M3 plate reader.

FIG. 1 shows the ELISA analysis of BL72 antibodies purified using the method detailed above. Antibodies eluted in fractions E1 and E2 were combined and used for further immunoassays.

Example 4

Cross Reactivity of pHis and pTyr Antibodies

The cross-reactivity of pHis antibodies raised against pPye was determined using a dot blot analysis. Various concentrations of a peptide sequence were added to a filter, which was then probed with pHis (top) or pTyr (middle). Protein loading was verified using colloidal gold staining (bottom).

Each peptide from the library shown in FIG. 2B was combined for His, pHis, pSer, pThr, or pTyr peptide samples, and serially diluted to 300, 150, 75, 33, and 16.7 ☐ M total peptide in MQ-$H_2O$. 3 ☐ L from each diluted sample was spotted onto a nitrocellulose membrane to give 900, 450, 225, 100, and 50 pmol of total peptide. The membrane was then either analyzed by Western blot or colloidal gold staining.

For Western blotting, the membrane was incubated in TBST (pH 8.5) with 3% BSA for 1 hr. The membrane was then incubated with affinity purified pHis antibody or monoclonal pTyr antibody that was diluted 1:250 (pHis) or 1:500 (pTyr) in TBST with 3% BSA for 1 hr. The membrane was then washed three times with TBST for 5 minutes each and then incubated with secondary antibody (Li-Cor, goat anti-rabbit 800CW for pHis, or goat-anti mouse 680RD for pTyr) for 1 hr in TBST with 3% BSA. The membrane was then washed 3 times with TBST for 5 minutes each and then washed 3 times with MQ-$H_2O$ for 10 seconds each. The membrane was then imaged using a Li-COR Odyssey infrared imager. To serve as a loading control, a similarly spotted membrane that was not used in the Western blot protocol was stained with Colloidal gold following the manufacturer's instructions.

FIG. 2 shows the results of a dot blot analysis of a phosphopeptide library consisting of different peptides that contain either a phosphohistidine (pHis), Histidine (His), phosphoserine (pSer), phosphothreonine (pThr), or phosphotyrosine (pTyr) residue in the sequence. The specific sequences in the library are depicted in FIG. 2B.

A known anti-pTyr antibody (4G10, Millipore) selectively recognized the pTyr-containing peptides. As a loading control, the membranes were stained with colloidal gold to show that roughly equal amounts of peptides were loaded onto the membrane.

The dot blot analysis shows that the pHis antibodies raised against pPye (BL72) are highly selective for pHis peptides and do not recognize other phosphopeptide types or non-phosphorylated peptide sequences under these conditions. The BL72 antibody shows about 20-fold increased specificity towards the pHis peptide over the pTyr peptide.

Example 5

Comparative Binding Affinity of Anti-Sera to pPye

For the pHis antibody to be useful, it should show higher affinity for pHis proteins relative to their non-phosphorylated counterparts. The specificity of the anti sera raised against pPye was thus determined.

Figure 3A:
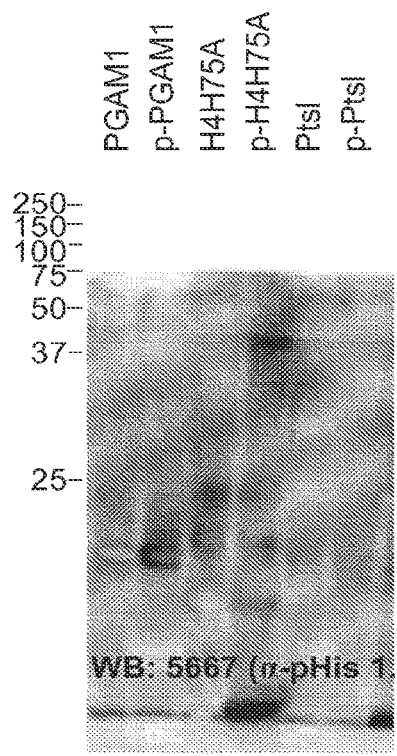
FIG. 3A-C shows a Western blot analysis of different purified pHis-containing proteins (PGAM1, Histone H4, PtsI) using two different rabbit crude anti-sera (BL72 and H70) raised against pPye. Proteins were analyzed with or without phosphorylation. A) Crude anti-serum from antibodies raised against pTze (□-pHis 1.0). B) Anti-pHis (BL72). C) Anti-pHis (H70).
Figure 3B:
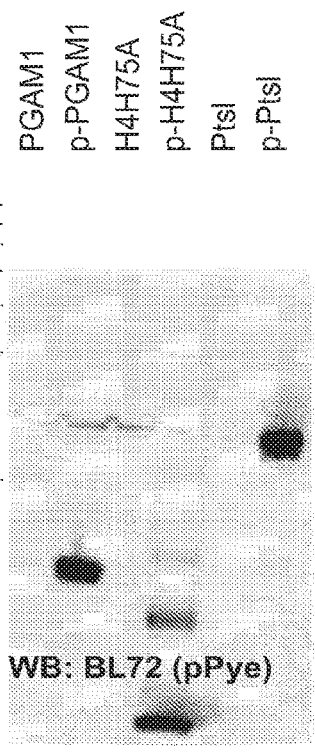
Figure 3C:
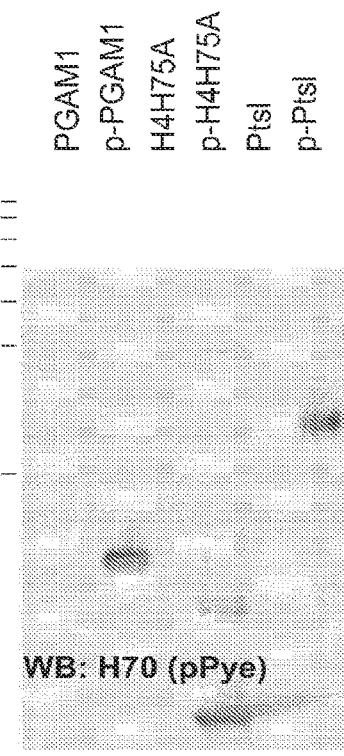

FIG. 3 shows the results of Western blot analyses when antisera raised against pTze (☐ 1-pHis1.0 see Kee et al., Nature Chem. Biol. 9:416-421 (2013) and WO 2012/040525) was compared to binding of two different rabbit crude antisera against pPye (BL72 and H70) against PGAM1, histidine phosphorylated PGAM1 (p-PGAM1), Histone H4 (H4H75A), histidine phosphorylated Histone H4 (p-H4H75A), PtsI, and histidine phosphorylated PtsI (p-PtsI). Much higher phosphorylation-dependent binding was observed with the pPye elicited antisera.

In FIG. 4, binding of antisera raised against pTze (☐ 1-pHis1.0; see Kee et al., Nature Chem. Biol. 9:416-421 (2013) and WO 2012/040525) was compared to binding of two different rabbit crude antisera against pPye (BL72 and H70) in Western blot analysis against REX 293 cells lysed with RIPA buffer to give a whole cell lysate (293 RIPA Lys.), HEK 293 lysate incubated with hydroxylamine (HA) (293 RIPA Lys. +HA), which removes phosphate groups from phosphohistidine, lysate from NCM 3722 *E. coli* grown in glycerol (*E. coli* Glyc. Lys), NCM 3722. *E. coli* lysate treated with HA (*E. coli* Glyc. Lys +HA), Cytosolic HEK 293 lysate (293 Hyp. Lys.) and Cytosolic HEK 293 lysate treated with HA (293 Hyp. Lys, +HA)

Figure 4A:
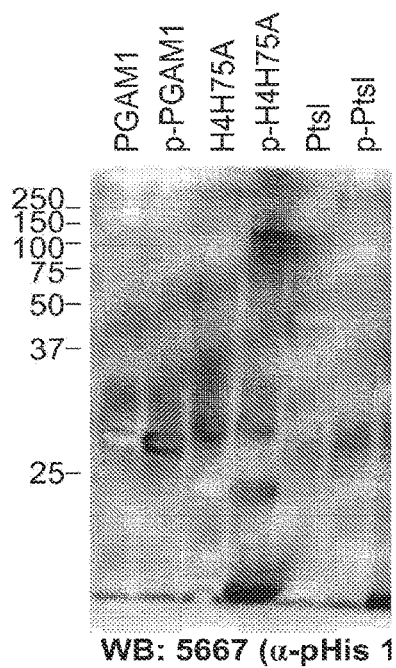
FIG. 4A-F shows Western blot analysis of mammalian whole cell lysate (293 RIPA Lys.), E. coli lysates from glycerol-fed E. coli (E. Coli Glyc. Lys.) and mammalian cytosolic lysate (293 Hyp. Lys.) using two different rabbit etude anti-sera (BL72 and 1-170) raised against pPye. A) Crude anti-serum from antibodies raised against a phosphoryltriazolyl mimic (Li-pHis 1.0). B) Anti-pHis (BL72). C) Anti-pHis (H70). D) Coomassie stain of A. E) Coomassie stain of B. F) Coomassie stain of C.
Figure 4B:
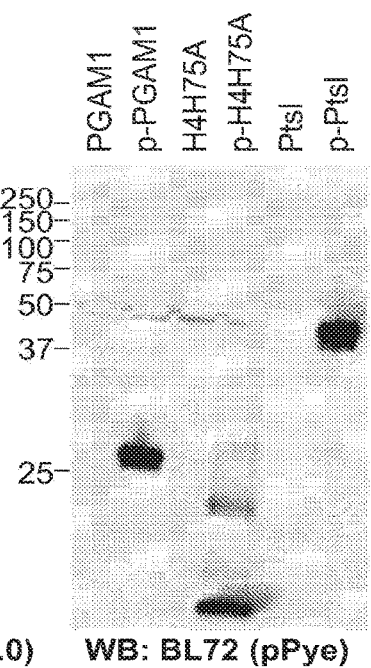
Figure 4C:
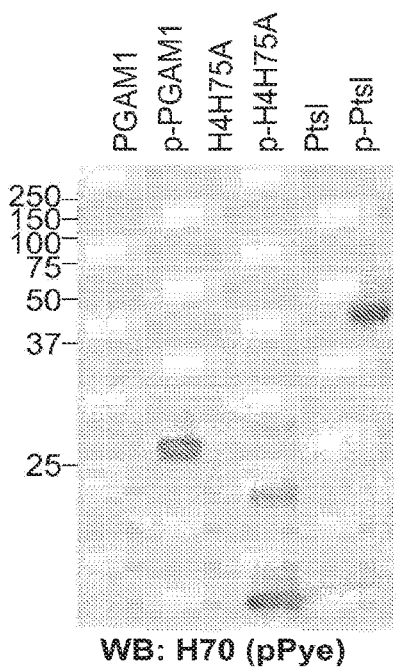
Figure 4D:
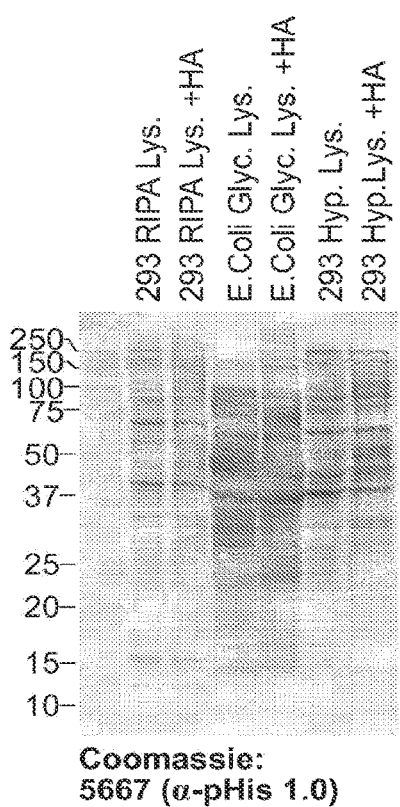
Figure 4E:
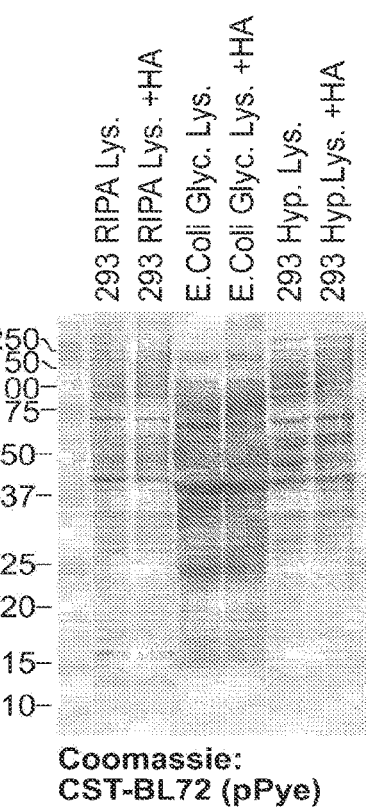
Figure 4F:
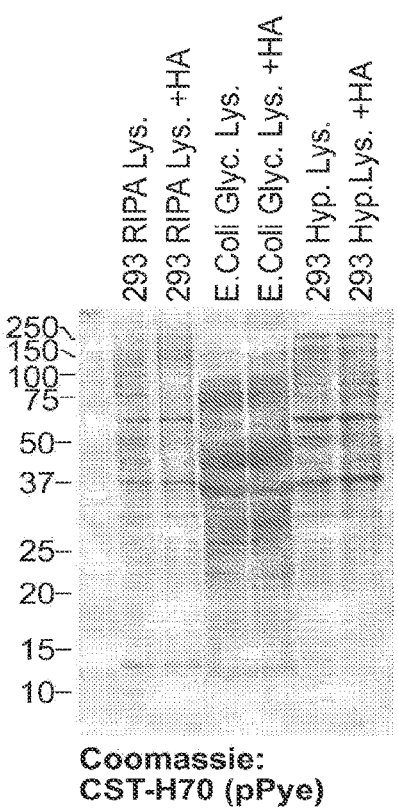

The antisera (BL72 and H70) show lower background in the HA treated samples compared to the ☐ 1-pHis1.0 antisera. In FIG. 4B, Coomassie blue staining confirmed that roughly equivalent amounts of protein were loaded in each lane.

Example 6 pPye-Elicited Antibodies Bind H4 Peptides

Relative binding of pHis antibodies elicited with pPye and binding of anti pTyr antibodies to a histone H4-derived peptide was compared.

In FIG. 5, various amounts of the H4-derived sequence Ac-CCGARKR XRKVLR-$NH_2$ (where X is pHis or pTyr) (SEQ ID NO:1) (0.5, 1.4, 4.2 12, 37, 111, and 333 pmole) were spotted in duplicate on a membrane and probed with pPye-elicited antisera. The pPye-elicited antibodies were 20-fold more selective for pHis than for pTyr. In contrast, parallel studies using an antisera raised against pTze (pHis Ab v1.0; see Kee et al., Nature Chem. Biol. 9:416-421 (2013 and WO 2012/040525)) was only 10-fold more selective for pHis than for than pTyr.

Example 7

Detection of Phosphorylation States in Bacterial Virulence Mutants

For the antibody to be a diagnostic in detecting bacterial virulence, sporulation, infection, and/or biofilm formation, it is important to detect changes in phosphorylation levels on histidine kinases.

The ability to detect virulence mutants is demonstrated using *Staphylococcus aureus* AgrC. Phosphorylated histidine is detected on AgrC histidine kinase from a *Staphylococcus aureus*, in which AgrC becomes autophosphorylated on a histidine residue in the presence of ATP.

AgrC and ATP are mixed in vitro, and an anti-pHis antibody as described herein is used to detect phosphorylation. In addition, endogenous phosphorylation of AgrC expressed in *E. coli* and isolated out the cell membranes are also detected. The active forms of AgrC (R238H and wt-AgrC) are detected but not the inactive histidine mutant of AgrC (H239Q). Similarly, it is further predicted that histidine phosphorylation is detected of KinB treated with ATP but not on KinB without ATP treatment or KinB treated with ATP and then with HA to remove the phosphorylated residue.

Example 8

Anti-Phosphohistidine Antibodies Detect Metabolic Changes in Bacteria

For the antibody to be a diagnostic in detecting bacterial virulence, sporulation, infection, and/or biofilm formation, it is important that the antibodies can detect metabolic changes in the bacteria.

NCM 3722 *E. coli* are grown for 3 hours (3 h) or overnight (O/N) in different carbon sources. The cells are then lysed and analyzed by Western blot for pHis levels. A Coomassie stained membrane is used as a loading control.

Growing the *E. coli* on different carbon sources leads to changes in the metabolic activity of *E. coli*, which are detected by the anti-phosphohistidine antibodies as described herein.

Additional embodiments are within the claims.

What is claimed is:

1. A phosphonopyrazole of formula I:

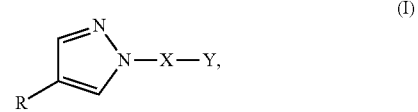

wherein:

R is

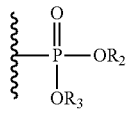

$R_2$, and $R_3$, are each, independently, H or alkyl;

X is —$CH_2$—$CH_2$—;

Y is NHBoc, where Boc is tert-butoxycarbonyl protecting group.

* * * * *